US012797195B2

(12) United States Patent
Zhao et al.

(10) Patent No.: US 12,797,195 B2
(45) Date of Patent: Nov. 17, 2026

(54) RING CONTRACTION APPARATUS FOR MITRAL VALVE ANNULUS

(71) Applicant: SHANGHAI SHAPE MEMORY ALLOY CO., LTD., Shanghai (CN)

(72) Inventors: Yang Zhao, Shanghai (CN); Xiaojian Liu, Shanghai (CN); Yuxin Zhang, Shanghai (CN)

(73) Assignee: SHANGHAI SHAPE MEMORY ALLOY CO., LTD., Shanghai (CN)

( * ) Notice: Subject to any disclaimer, the term of this patent is extended or adjusted under 35 U.S.C. 154(b) by 429 days.

(21) Appl. No.: 18/562,655

(22) PCT Filed: May 21, 2021

(86) PCT No.: PCT/CN2021/095110

§ 371 (c)(1),
(2) Date: Nov. 20, 2023

(87) PCT Pub. No.: WO2022/241755

PCT Pub. Date: Nov. 24, 2022

(65) Prior Publication Data

US 2024/0238093 A1 Jul. 18, 2024

(51) Int. Cl.
*A61F 2/24* (2006.01)
*A61B 17/00* (2006.01)
(Continued)

(52) U.S. Cl.
CPC ........ *A61F 2/2466* (2013.01); *A61B 17/3478* (2013.01); *A61F 2/2454* (2013.01);
(Continued)

(58) Field of Classification Search
CPC .................. A61F 2/2466; A61F 2/2454; A61F 2230/0065; A61F 2/2457; A61B 17/3478;
(Continued)

(56) References Cited

U.S. PATENT DOCUMENTS 5,364,407 A 11/1994 Poll
2005/0125011 A1 6/2005 Spence et al.
(Continued)

FOREIGN PATENT DOCUMENTS

CN 107427296 A 12/2017
CN 109498216 A 3/2019
(Continued)

OTHER PUBLICATIONS

International Search Report and Written Opinion of the International Searching Authority dated Feb. 22, 2022 as received in Application No. PCT/CN2021/095110.
Extended European Search Report dated May 27, 2024 as received in Application No. 21940208.8.

*Primary Examiner* — Brooke Labranche
*Assistant Examiner* — Rachael L Geiger
(74) *Attorney, Agent, or Firm* — Maschoff Brennan

(57) ABSTRACT

A ring contraction apparatus for a mitral valve annulus, comprising at least two fixing mechanisms, a piercing mechanism and a locking mechanism. Each fixing mechanism comprises a fixing knot and a traction wire, the traction wire is mounted on the fixing knot, and two ends of the traction wire are located outside a proximal end of the fixing knot. The piercing mechanism is used for piercing the fixing knots and the traction wires of the fixing mechanisms onto an annulus, so that the fixing knots are located on one side of the annulus and the two ends of the traction wire are located on the other side of the annulus. Traction wires of two adjacent fixing mechanisms are driven by traction forces to approach each other so as to shorten the distance between two adjacent fixing knots.

17 Claims, 13 Drawing Sheets

(51) Int. Cl.
*A61B 17/34* (2006.01)
*A61M 25/00* (2006.01)

(52) U.S. Cl.
CPC ............... *A61B 2017/00862* (2013.01); *A61F 2230/0065* (2013.01); *A61M 2025/0095* (2013.01)

(58) Field of Classification Search
CPC ........... A61B 2017/00862; A61B 2017/00243; A61B 2017/0496; A61B 17/0487; A61B 2017/0406; A61B 2017/0409; A61B 2017/0417; A61B 2017/0488; A61B 17/0401; A61M 2025/0095
See application file for complete search history.

(56) References Cited

U.S. PATENT DOCUMENTS

| | | | | |
|---|---|---|---|---|
| 2007/0244557 | A1 | 10/2007 | Rafiee et al. | |
| 2008/0228165 | A1 | 9/2008 | Spence et al. | |
| 2014/0188140 | A1 | 7/2014 | Meier et al. | |
| 2018/0214269 | A1 * | 8/2018 | Wilson ............... | A61B 17/0401 |
| 2018/0289480 | A1 | 10/2018 | D'ambra et al. | |

FOREIGN PATENT DOCUMENTS

| | | | |
|---|---|---|---|
| CN | 109498217 | A | 3/2019 |
| EP | 2 977 013 | B1 | 8/2019 |
| WO | 2016/148714 | A1 | 9/2016 |

* cited by examiner

RING CONTRACTION APPARATUS FOR MITRAL VALVE ANNULUS

TECHNICAL FIELD

The present application belongs to the technical field of medical apparatuses, and particularly relates to a ring contraction apparatus for a mitral valve annulus.

BACKGROUND

The human heart has four chambers and also has four valves, which are a mitral valve, a tricuspid valve, an aortic valve and a pulmonary valve respectively. The mitral valve is located between a left atrium and a left ventricle and guarantees, like a one-way valve, that blood circulation flows from the left atrium to the left ventricle by a certain flow amount. The mitral valve is composed of five parts, namely valve leaflet, an annulus, a papillary muscle, chordae tendineae and a commissure. When the mitral valve is closed normally, two valve leaflets are located on the same plane and closed tightly, so that blood reflux of the left ventricle can be completely blocked. Functional completeness of the mitral valve requires an appropriate size of a mitral valve annulus, a complete structure of valve leaflets, papillary muscle contraction for stretching the chordae tendineae to play a formation role of the valve leaflets, muscle contraction of the left ventricle for producing an appropriate close force and normal ventricular form and function. Reflux of the mitral valve may be caused if any one of these factors is abnormal, and blood flows back to the left atrium from the left ventricle.

With social development and aging of population, an incidence rate of mitral valve reflux is in a tendency of obvious increase, the mitral valve reflux has become a common heart valve disease at present, which is mainly caused by incomplete closing of the mitral valve annulus, and thus a ring contraction apparatus for repair of incomplete closing of the mitral valve annulus needs to be provided.

SUMMARY OF THE INVENTION

Thus, a technical problem to be actually solved by the present application is to provide a ring contraction apparatus for repair of incomplete closing of a mitral valve annulus.

As such, a ring contraction apparatus for a mitral valve annulus provided by the present application includes:

at least two fixing mechanisms; wherein any one of the fixing mechanisms includes a fixing knot and a traction wire, the traction wire is mounted on the fixing knot, and two ends of the traction wire are located outside a proximal end of the fixing knot;

a puncturing mechanism, used for puncturing the fixing knot and the traction wire of any one of the fixing mechanisms into the annulus, so that the fixing knot is located on one side of the annulus and two ends of the traction wire are located on the other side of the annulus, wherein the traction wires of the two adjacent fixing mechanisms are driven by a traction force to approach each other so as to shorten a distance between the two adjacent fixing knots; and a locking mechanism, used for locking ends of the traction wires in the two adjacent fixing mechanisms onto the annulus in a case that the traction wires of the two adjacent fixing mechanism are pulled in place.

Optionally, in the ring contraction apparatus for the mitral valve annulus, the locking mechanism includes:

a locking body, having a first channel extending in a length direction of the locking body; and a locking plug, inserted into the first channel so as to clamp the traction wires between the locking plug and the locking body.

Optionally, in the ring contraction apparatus for the mitral valve annulus, a locking hole through which the ends of the traction wires pass is formed in a side wall of the locking body.

Optionally, in the ring contraction apparatus for the mitral valve annulus, a first mounting hole is also arranged in the side wall of the locking body;

the locking mechanism further includes at least one elastomer, a proximal end of the elastomer is formed in the first mounting hole, and a far end of the elastomer tends to extend into the first channel under an action of its own deformation amount; and the elastomer swings towards an inside of the first mounting hole under an extrusion force of an outer wall of the locking plug in a case that the locking plug is inserted towards the first channel, and after the locking plug crosses the far end of the elastomer, the elastomer is restored and the far end of the elastomer is blocked onto the locking plug.

Optionally, in the ring contraction apparatus for the mitral valve annulus, the locking plug includes a base and a first annular boss formed on a periphery of a far end of the base, and the first annular boss applies an extrusion force to the elastomer; and the far end of the elastomer is blocked onto a side of a proximal end of the first annular boss in a case that the elastomer is restored.

Optionally, in the ring contraction apparatus for the mitral valve annulus, a second annular boss protruding inwards is arranged on an inner wall of a far end of the locking body;

a far end of the first annular boss is maintained between the second annular boss and the elastomer under blocking of the second annular boss; and/or the elastomer is an elastic piece.

Optionally, in the ring contraction apparatus for the mitral valve annulus, the locking mechanism further includes a conveying mechanism; the conveying mechanism includes an outer tube, a hanging sheath slidably arranged in the outer tube and a push inner tube slidably arranged in the hanging sheath;

a far end of the hanging sheath is detachably connected with a proximal end of the locking body, and a far end of the push inner tube is inserted into or is in sleeving fit with a proximal end of the locking plug; and both the locking body and the locking plug are located in the outer tube before the locking body is released.

Optionally, in the ring contraction apparatus for the mitral valve annulus, the puncturing mechanism includes:

an outer sheath;

a puncture needle, slidably arranged in the outer sheath, wherein a notch channel extending in a length direction of the puncture needle is arranged on an outer wall of a far end of the puncture needle; and a push sheath, slidably arranged in the outer sheath and sleeving the puncture needle; wherein the fixing knots have a folded state of being folded into the outer sheath and a released state of being punctured onto the annulus;

in the folded state, the fixing knots sleeve an outer wall of the notch channel of the puncture needle, a proximal end of the puncture needle and a far end of the push sheath are distributed oppositely, a first end of each traction wire is located in the notch channel, and a second end of the traction wire passes through the notch channel, then is winded onto an outer wall of the fixing knot from a far end of the fixing knot and extends into the puncture needle via a proximal end of the notch channel so as to overlap the first end and the second end; and in the released state, the traction wires sleeve side walls of the fixing knots and are punctured onto the annulus, and the fixing knots bend to form a ring under traction of the traction wires.

Optionally, in the ring contraction apparatus for the mitral valve annulus, a notch sinking inwards is formed in a side wall of the notch channel of the puncture needle; and in the folded state, the far ends of the fixing knots sleeve the notch, and the second ends of the traction wires are winded on the outer walls of the fixing knots after passing through the notch.

Optionally, in the ring contraction apparatus for the mitral valve annulus, each fixing knot is in a spiral shape or a round tube shape; and/or a fixing head end is arranged on an end face of a far end of the outer sheath and is in a trumpet shape from its proximal end to its far end.

The technical solutions of the present application have the following advantages.

1. The present application provides the ring contraction apparatus for the mitral valve annulus, including at least two fixing mechanisms, the puncturing mechanism and the locking mechanism. Each fixing mechanism includes the fixing knot and the traction wire, the traction wire is mounted on the fixing knot, and two ends of the traction wire are located outside the proximal end of the fixing knot. The puncturing mechanism is used for puncturing the fixing knots and the traction wires of the fixing mechanisms onto the annulus, so that the fixing knots are located on one side of the annulus and the two ends of the traction wire are located on the other side of the annulus. Traction wires of two adjacent fixing mechanisms are driven by a traction force to approach each other so as to shorten a distance between two adjacent fixing knots, so that an annulus portion between the two adjacent fixing knots is bent or creased, a circumferential length of the annulus is reduced, and the size of an inner hole of the annulus is reduced. Once the distance between the two fixing knots is adjusted in place, the locking mechanism is used to lock end parts of the traction wires in the two adjacent fixing mechanisms to the annulus, so that the annulus is kept in a state in which the inner hole is shrunken, and the annulus is closed more easily due to reduced size of the inner hole of the annulus, thereby solving the problem of incomplete closing of the annulus and achieving a repair effect.

2. In the ring contraction apparatus for the mitral valve annulus provided by the present application, the locking mechanism includes the locking body and the locking plug; the locking body has the first channel extending in the length direction of the locking body; and the locking plug is inserted into the first channel to clamp the traction wires between the locking plug and the locking body so that the traction wires of the two adjacent fixing mechanisms are locked and a distance between the two fixing knots is maintained.

3. In the ring contraction apparatus for the mitral valve annulus provided by the present application, the locking hole through which the ends of the traction wires pass is formed in the side wall of the locking body, so as to guarantee that when the locking plug slides in the first channel, the traction wires remain penetrating in the locking hole all the time and do not slide out of the first channel in a length direction of the first channel to further ensure a locking effect on the traction wires.

4. In the ring contraction apparatus for the mitral valve annulus provided by the present application, a first mounting hole is further formed in the side wall of the locking body; the locking mechanism further includes at least one elastomer, the proximal end of the elastomer is formed in the first mounting hole, and the far end of the elastomer tends to extend into the first channel under an action of an own deformation amount; and the elastomer swings towards an inside of the first mounting hole under an extrusion force of an outer wall of the locking plug in a case that the locking plug is inserted towards the first channel, and after the locking plug crosses the far end of the elastomer, the elastomer is restored and the far end of the elastomer is blocked onto the locking plug, so as to further guarantee that the locking plug, after being inserted in place, does not leave from the proximal end of the locking body despite moving with the mitral valve annulus.

BRIEF DESCRIPTION OF THE DRAWINGS

In order to more clearly describe specific implementations of the present application or technical solutions in the prior art, accompanying drawings needing to be used in the description of the specific implementations or the prior art will be briefly introduced below. Apparently, the accompanying drawings in the following description are some implementations of the present application. Those ordinarily skilled in the art may also obtain other accompanying drawings according to these accompanying drawings without making creative efforts.

DESCRIPTIONS OF REFERENCE NUMERALS

- 1—puncturing mechanism; 11—fixing head end; 12—puncture needle; 121—notch channel; 122—notch; 13—outer sheath; 14—fixing knot; 15—traction wire; 16—push sheath;
- 2—locking mechanism; 21—locking body; 211—second annular boss; 212—notch groove; 213—first mounting hole; 22—locking plug; 221—first annular boss; 222—base;
- 23—hanging sheath; 24—outer tube; 25—push inner tube; 26—elastomer; 27—locking hole; and 3—mitral valve annulus.

DETAILED DESCRIPTION

The technical solutions of the present application will be clearly and completely described in the following with reference to the accompanying drawings. Apparently, the described embodiments are merely some rather than all of the embodiments of the present application. All other embodiments obtained by those ordinarily skilled in the art based on the embodiments of the present application without making creative efforts fall within the protection scope of the present application.

In description of the present application, it needs to be noted that unless otherwise specified and limited clearly, terms "mount", "connect" and "connection" are to be understood in a broad sense, for example, it may be a fixed connection, a detachable connection or an integrated connection; and it may be a direct connection, an indirect connection through an intermediate medium or communication between interiors of two elements. Specific meanings of the above terms in the present application may be understood by those ordinarily skilled in the art according to specific conditions.

Besides, technical features involved in different implementations of the present application described below may be combined mutually without a conflict between one another.

Embodiment 1

This embodiment provides a ring contraction apparatus for a mitral valve annulus, as shown in FIG. 1 to FIG. 13, including at least two fixing mechanisms, a puncturing mechanism 1 and a locking mechanism 2.

Figure 11A:
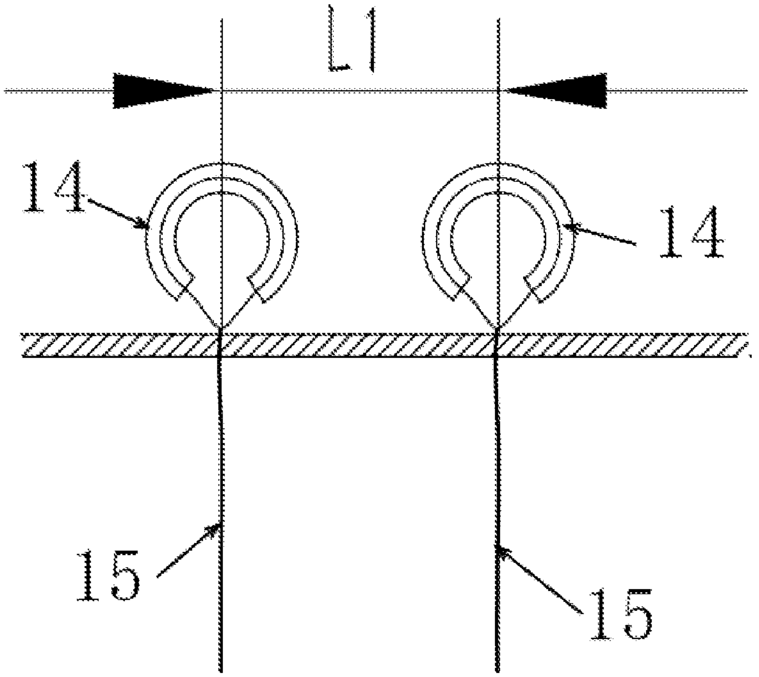
FIG. 11*a* is a schematic diagram of a state that a ring contraction apparatus for a mitral valve annulus is punctured into the annulus and not locked.
Figure 11B:
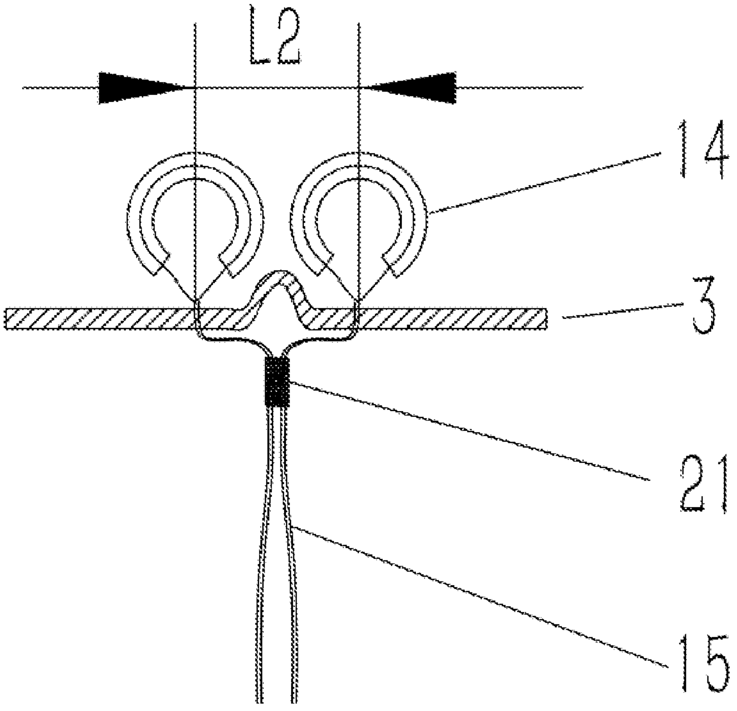
FIG. 11*b* is a schematic diagram of a state that a ring contraction apparatus for a mitral valve annulus is punctured into the annulus and locked.

Any one of the fixing mechanisms includes a fixing knot 14 and a traction wire 15, the traction wire 15 is mounted on the fixing knot 14, two ends of the traction wire 15 are located outside a proximal end of the fixing knot 14, the puncturing mechanism 1 is used for puncturing the fixing knot 14 and the traction wire 15 of any one of the fixing mechanisms onto an annulus, so that the fixing knot 14 is located on one side (for example, located on a side of a left atrium) of the annulus and the two ends of the traction wire are located on the other side (for example, located on a side of a left ventricle) of the annulus, as shown in FIG. 11*a*. Traction wires 15 of two adjacent fixing mechanisms are driven by a traction force to approach each other so as to shorten a distance between two adjacent fixing knots 14, so that an annulus portion between the two adjacent fixing knots 14 is bent or creased, a circumferential length of the annulus is reduced, as shown in FIG. 11*b*, and thus a size of an inner hole of the annulus is reduced; and after the distance between the two fixing knots 14 is adjusted in place, the locking mechanism 2 is used to lock end parts of the traction wires 15 in the two adjacent fixing mechanisms to the annulus, so that the annulus is kept in a state in which the inner hole is shrunken, and as the size of the inner hole of the annulus is reduced, the annulus is closed more easily, thereby solving the problem of incomplete closing of the annulus and achieving a repair effect.

Figure 5:
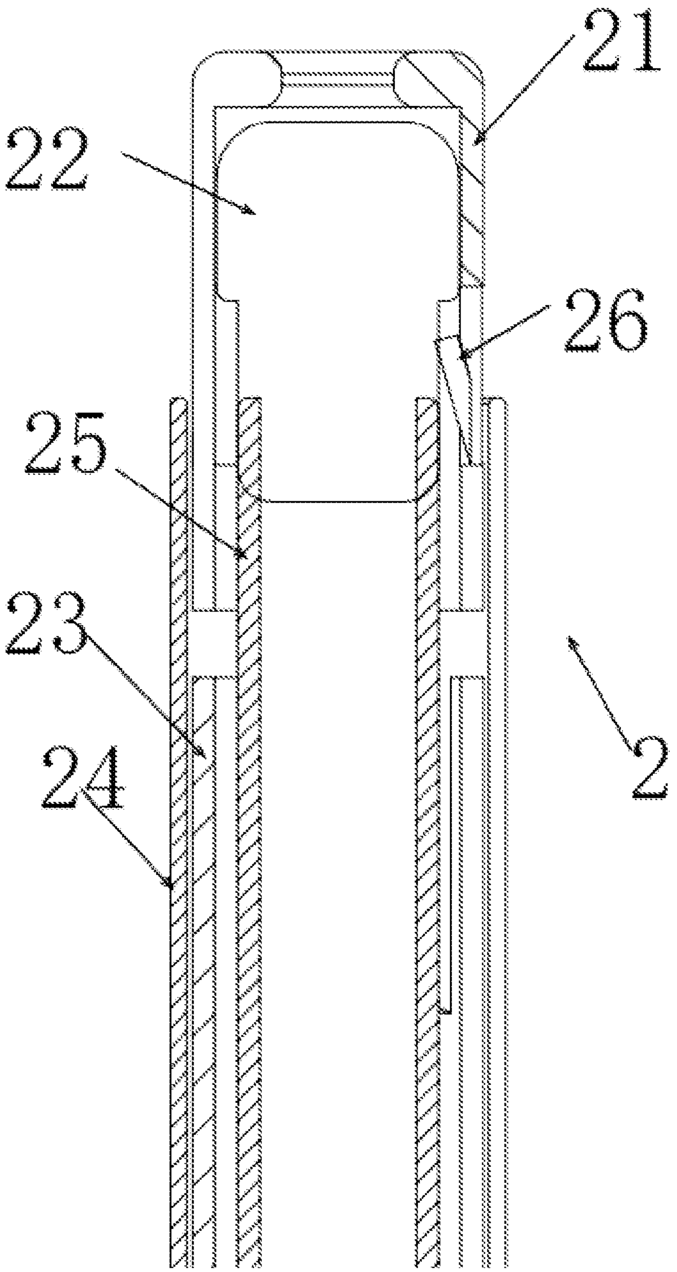
FIG. 5 is a sectional view of a locking mechanism in Embodiment 1 of the present application.

As for the locking mechanism 2, preferably, as shown in FIG. 5, the locking mechanism 2 includes a locking body 21 and a locking plug 22. The locking body 21 has a first channel extending in a length direction of the locking body; the locking plug 22 is inserted into the first channel so as to clamp the traction wires 15 between the locking plug 22 and the locking body 21, at the moment, the two ends of the traction wires 15 need to extend out of a proximal end of the locking body 21, so as to lock the traction wires 15 onto the locking body 21, and the adjusted distance between the two fixing knots 14 remains. During locking, the locking plug 22 only needs to be inserted into the locking body 21 from a proximal end to a far end.

Figure 7:
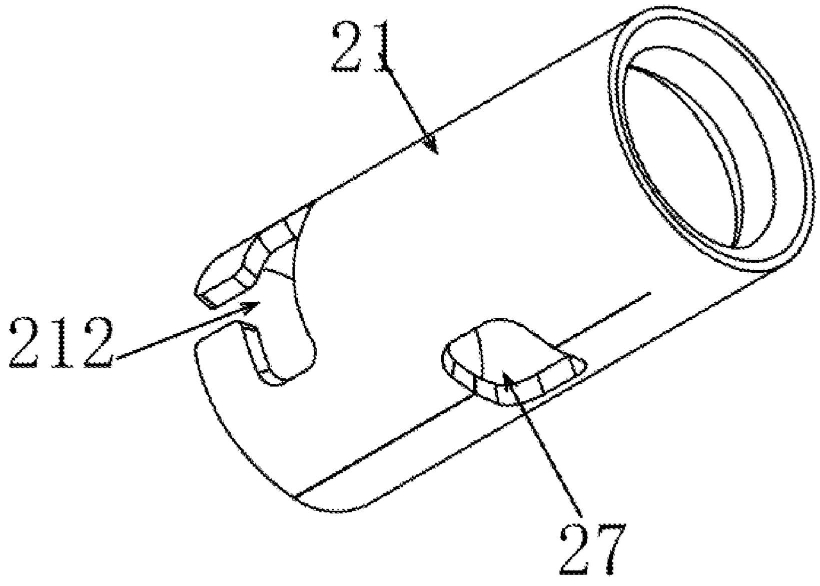
FIG. 7 is a schematic structural diagram of the locking body in FIG. 5.

Further preferably, as shown in FIG. 7, a locking hole 27 through which the ends of the traction wires 15 pass is formed in a side wall of the locking body 21. Before the locking plug 22 is inserted into the locking body 21, the two ends of the traction wires 15 pass through the locking hole 27 after passing through the first channel and then adjust the distance between the two fixing knots 14 by applying a traction force to the traction wires 15, after the distance is adjusted in place, the locking plug 22 is inserted into the locking body 21, and by forming the locking hole 27, the two ends of the traction wires 15 do not need to extend out of the proximal end of the first channel and only need to extend out of the locking hole 27, which is also convenient for applying the traction force to the traction wires 15.

Figure 6:
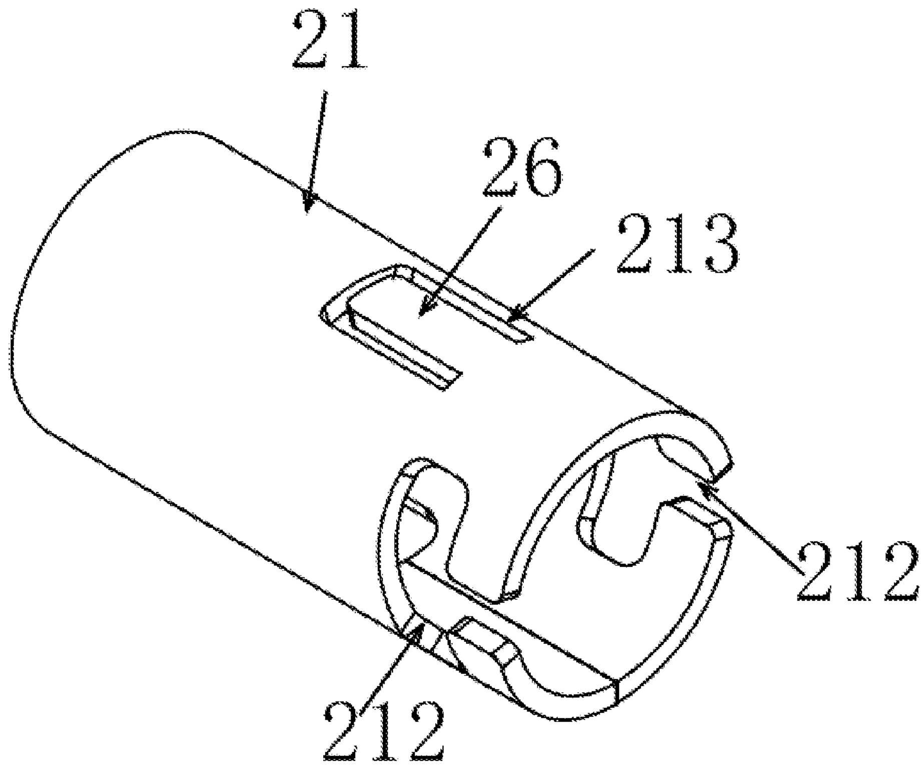
FIG. 6 is a schematic structural diagram of a locking body in FIG. 5.
Figure 8A:
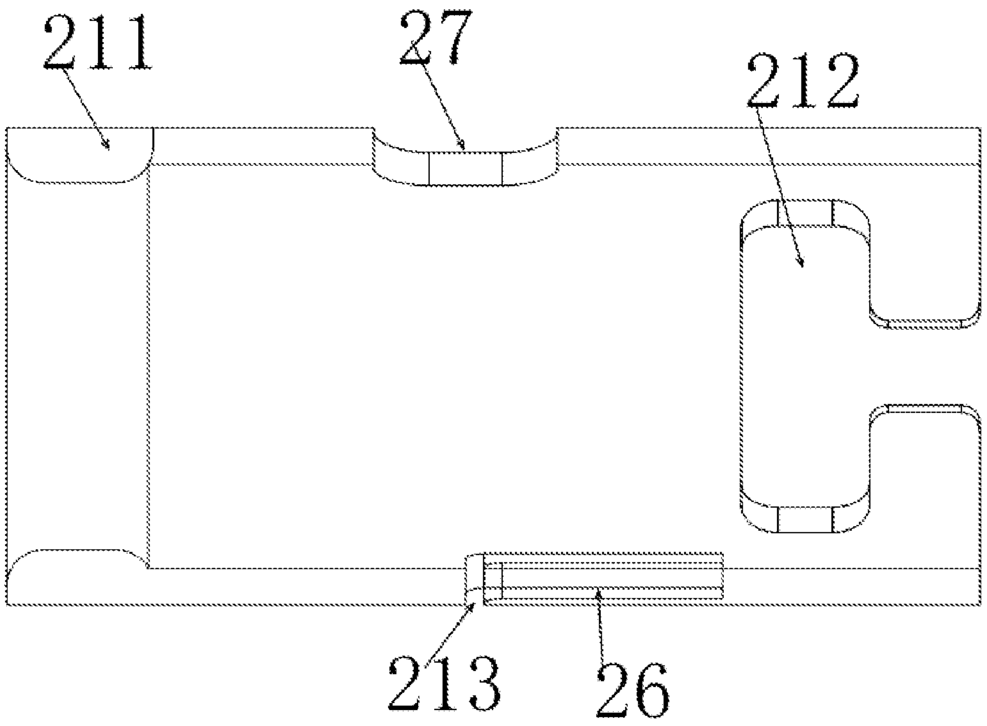
FIG. 8*a* is a schematic sectional view of the locking body in FIG. 5.

Further preferably, as shown in FIG. 8*a* and FIG. 6, a first mounting hole 213 is also formed in the side wall of the locking body 21; the locking mechanism 2 further includes at least one elastomer 26, a proximal end of the elastomer 26 is formed in the first mounting hole 213, and a far end of the elastomer tends to extend into the first channel under an action of an own deformation amount; and the elastomer 26 swings towards an inside of the first mounting hole 213 under an extrusion force of an outer wall of the locking plug 22 in a case that the locking plug 22 is inserted towards the first channel, and after the locking plug 22 crosses the far end of the elastomer 26, the elastomer 26 is restored and the far end of the elastomer is blocked onto the locking plug 22, so as to limit the proximal end of the locking plug 22 onto the locking body 21 and avoid sliding out from the proximal end of the locking body 21.

Figure 9:
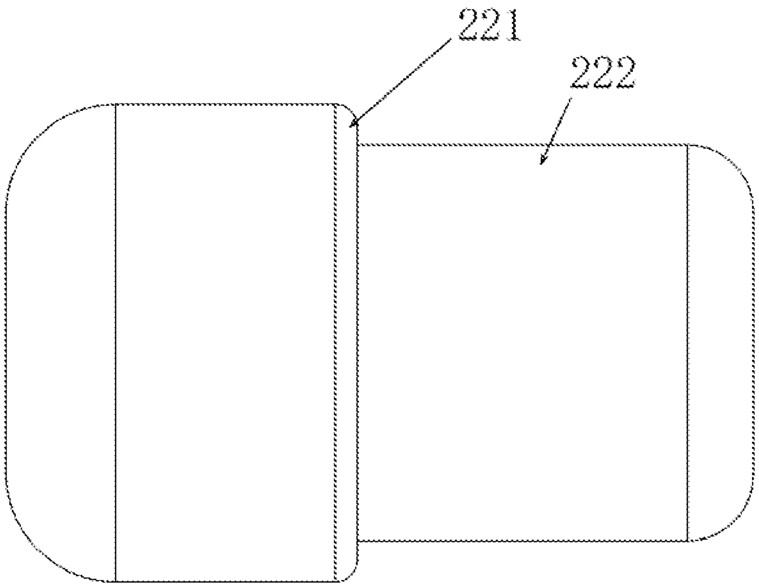
FIG. 9 is a schematic structural diagram of a locking plug in FIG. 5.

Specifically, as shown in FIG. 9, the locking plug 22 includes a base 222 and a first annular boss 221 formed on a periphery of a far end of the base 222, and the first annular boss 211 applies an extrusion force to the elastomer 26; and the far end of the elastomer 26 is blocked onto a side of a proximal end of the first annular boss 221 in a case that the elastomer 26 is restored, so as to achieve a blocking force for the locking plug 22. As a variation, only the far end of the base 222 and the first annular boss 221 may also be arranged, and an end surface of the first annular boss 221 is used as a proximal end surface of the locking plug 22.

The locking body 21 and the elastomer 26 are integrally formed, preferably, a nickel-titanium alloy material, or other medical deformable alloy material or a memory alloy material is used. As for the elastomer 26, preferably, the elastomer 26 is an elastic piece or a spring.

As for a material of the locking plug 22, preferably, a rubber material is used for forming a rubber plug, or another medical high molecular material is used.

Figure 8B:
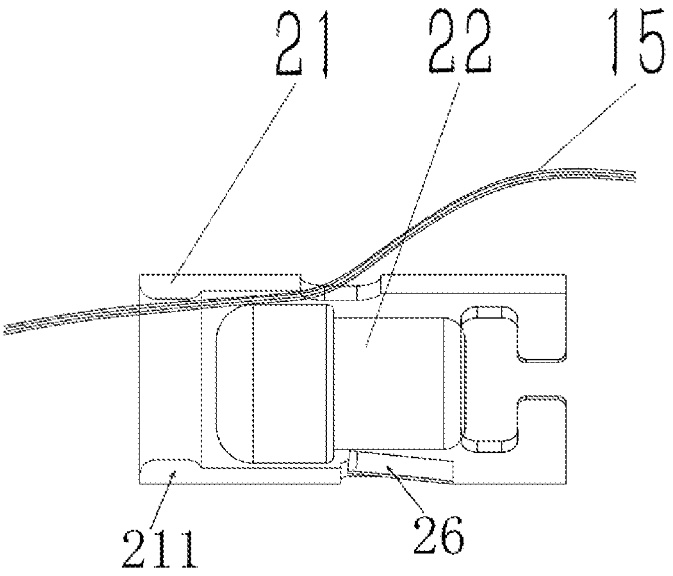
FIG. 8*b* is a schematic sectional view after the locking body in FIG. 8*a* matches traction wires.

Further preferably, as shown in FIG. 8*a* and FIG. 8*b*, a second annular boss 211 protruding inwards is arranged on an inner wall of the far end of the locking body 21; and a far end of the first annular boss 221 is maintained between the second annular boss 211 and the elastomer 26 under blocking of the second annular boss 211. That is, after the locking plug 22 slides in place on the locking body 21, under cooperation of the second annular boss 211 and the elastomer 26, the locking plug 22 is limited on the locking body 21, and the locking plug 22 cannot move relative to the locking body 21, so as to further guarantee the locking effect on the traction wires 15.

Shapes of the above first channel and the first mounting hole 213 are optimally round holes or certainly may also be holes in other shapes, such as, rectangular holes or elliptical holes or holes in other shapes.

Preferably, as shown in FIG. 5, the above locking mechanism 2 further includes a conveying mechanism 21 for conveying the locking body 21 and the locking plug 22; and the conveying mechanism includes an outer tube 24, a hanging sheath 23 slidably arranged in the outer tube 24 and a push inner tube 25 slidably arranged in the hanging sheath 23. A far end of the hanging sheath 23 is detachably connected with the proximal end of the locking body 21, and a far end of the push inner tube 25 is inserted into an inner hole of a proximal end of the locking plug 22 or sleeves the proximal end of the locking plug 22; and both the locking body 21 and the locking plug 22 are located in the outer tube 24 before the locking body 21 is not released.

Through movement of the outer tube 24, the whole conveying mechanism is transapically conveyed to nearby the mitral valve annulus, the outer tube 24 stops moving, the hanging sheath 23 pushes the locking body 21 to cause the locking body 21 to extend out of the far end of the outer tube 24, and the hanging sheath 23 is separated from the locking body 21. The ends of the traction wires 15 are punctured in the locking hole 27, the traction force is applied to the ends of the traction wires 15 so as to adjust the distance between the two fixing knots 14, after the distance between the two fixing knots 14 is adjusted in place, the push inner tube 25 pushes the locking plug to be inserted into the locking body 21, and then in view of the limiting effect of the elastomer 26, the push inner tube 25 is withdrawn and is separated from locking, and finally, the whole conveying mechanism is withdrawn from a human body by withdrawing the outer tube 24.

Preferably, as shown in FIG. 6, two notch grooves 212 which are in symmetric distribution are arranged on the proximal end of the locking body 21, and correspondingly, an ear hanger (not shown in Figure) suitable for being clamped into each ear hanger notch is arranged at the far end of the hanging sheath 23; before releasing, the ear hanger remains clamped into the notch grooves 212 under a radial restraining force of the outer tube 24; and when the hanging sheath 23 extends out of the outer tube 24, the ear hanger is restored under an action of an own deformation amount, tends to swing outwards and exit from the notch grooves 212, so that separation of the hanging sheath 23 from the locking body 21 is implemented.

Figure 1:
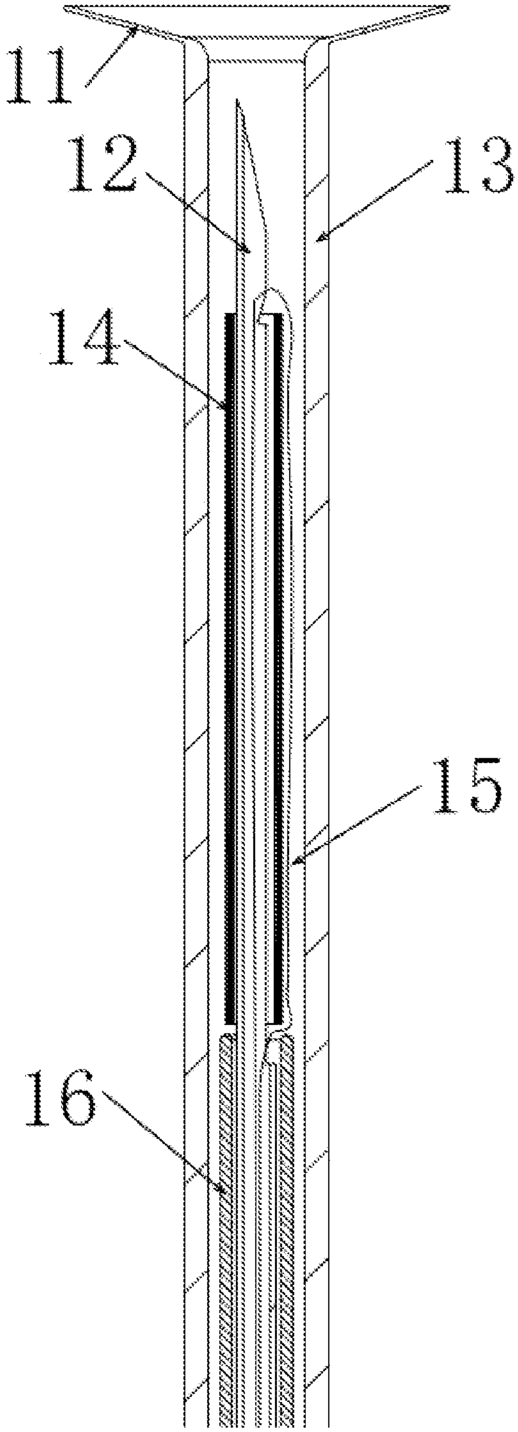
FIG. 1 is a sectional view of a puncturing mechanism of a ring contraction apparatus for a mitral valve annulus in Embodiment 1 of the present application.
Figure 2:
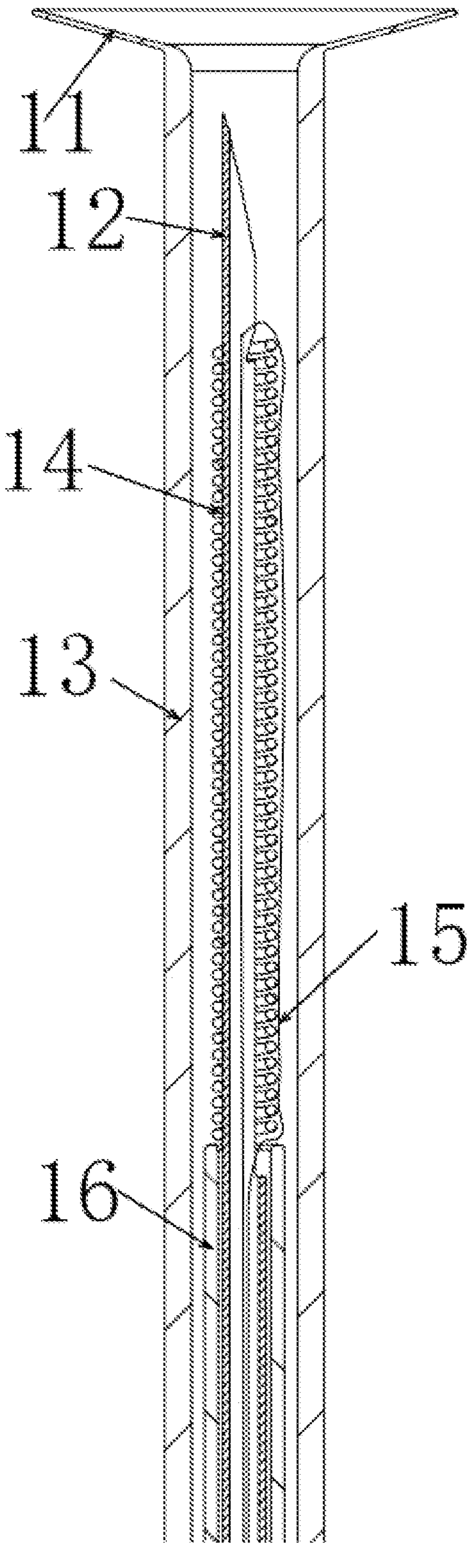
FIG. 2 is a sectional view of another implementation of a puncturing mechanism in Embodiment 1 of the present application.
Figure 3:
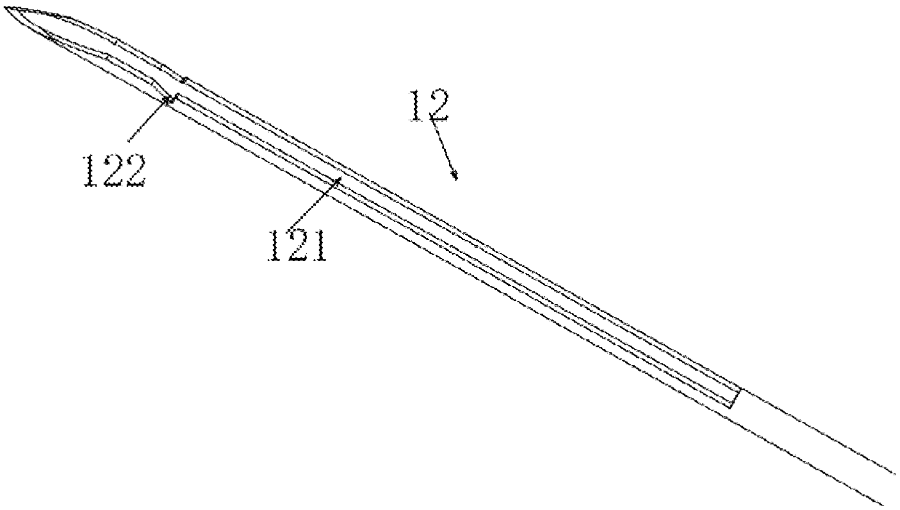
FIG. 3 is a schematic structural diagram of a puncture needle of t puncturing mechanism in FIG. 1.

As for the puncturing mechanism 1, as shown in FIG. 1, FIG. 2 and FIG. 3, the puncturing mechanism 1 includes an outer sheath 13, a puncture needle 12 and a push sheath 16. The puncture needle 12 is slidably arranged in the outer sheath 13, a notch channel 121 extending in a length direction of the puncture needle 12 is formed in an outer wall of a far end of the puncture needle 12, and the push sheath 16 is slidably arranged in the outer sheath 13 to sleeve the puncture needle.

The fixing knots 14 have a folded state of being folded into the outer sheath 13 and a released state of being punctured onto the annulus. In the folded state, as shown in FIG. 1 and FIG. 2, the fixing knots 14 sleeve an outer wall of the notch channel 121 of the puncture needle, a proximal end of the puncture needle and a far end of the push sheath 16 are distributed oppositely, a first end of each traction wire 15 is located in the notch channel 121, and a second end of each traction wire 15 passes through the notch channel 121, then is winded onto an outer wall of the fixing knot 14 from a far end of the fixing knot 14 and extends into the puncture needle via a proximal end of the notch channel 121 so as to overlap the first end and the second end; and end parts of the traction wires 15 which are in overlay distributed may extend out of the proximal end of the puncture needle, so that an operator conveniently applies the traction force to the traction wires 15; or the first end and the second end are distributed in the puncture needle, connected with an operating mechanism and applying the traction force to the traction wires 15.

Figure 4A:
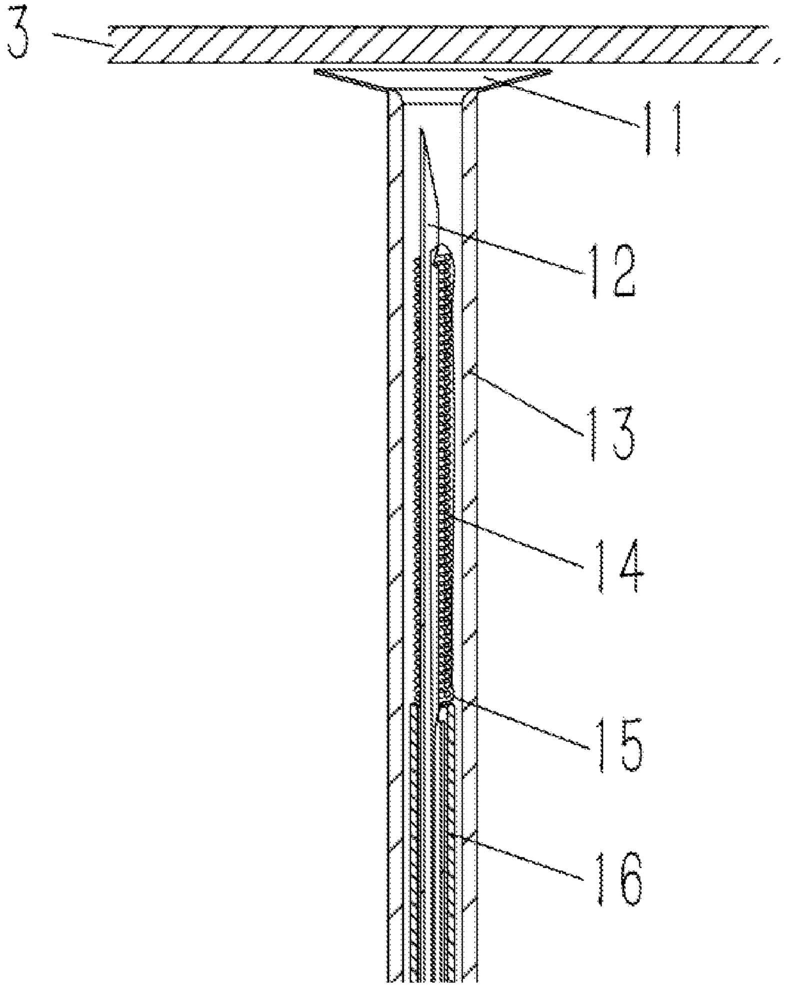
FIG. 4*a* is a schematic diagram of a state of a fixing head end fixed onto an annulus of the puncturing mechanism in FIG. 1.
Figure 4B:
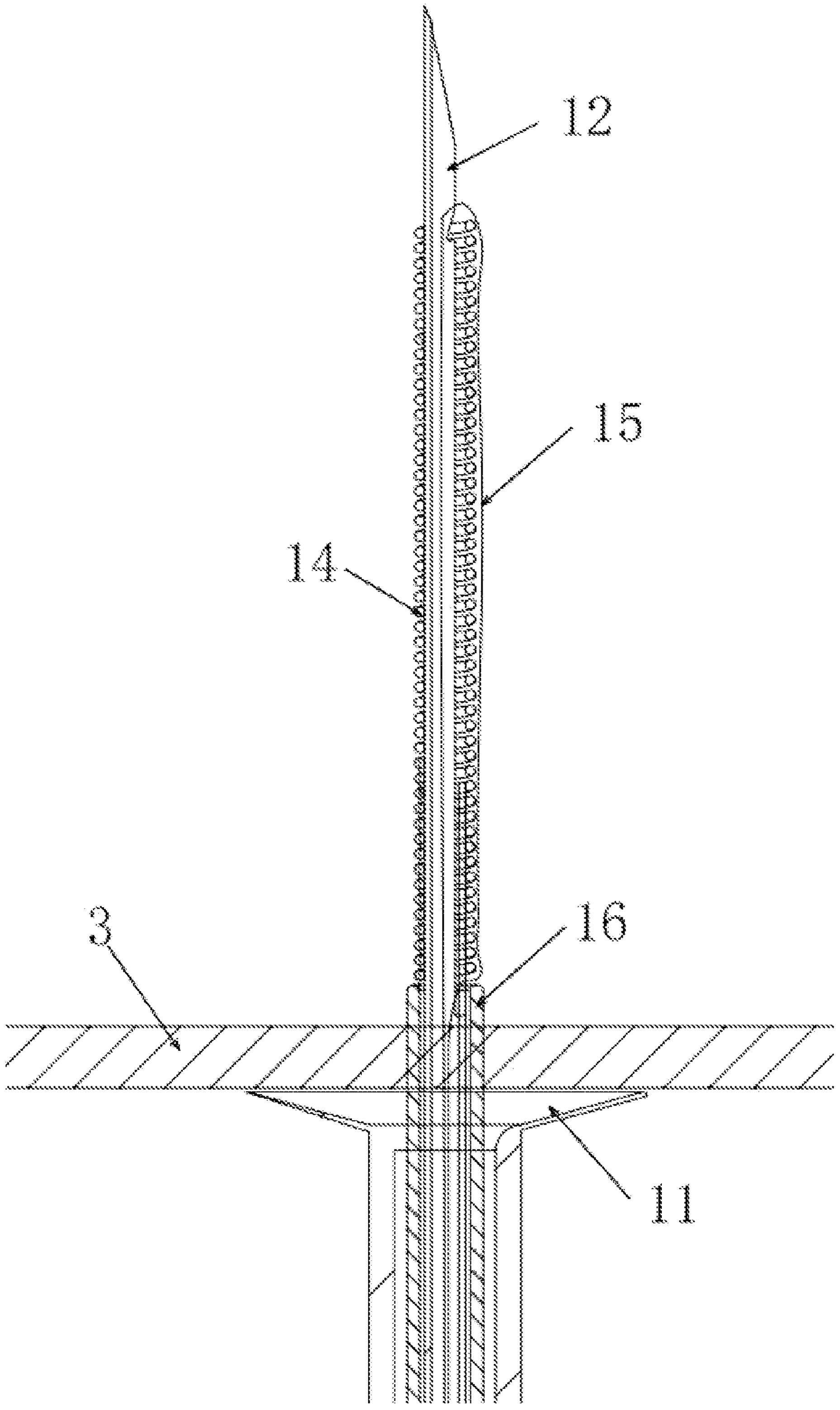
FIG. 4*b* is a schematic diagram of a state after a puncture needle, a push sheath and fixing knots of the puncturing mechanism in FIG. 1 are punctured into the annulus.
Figure 4C:
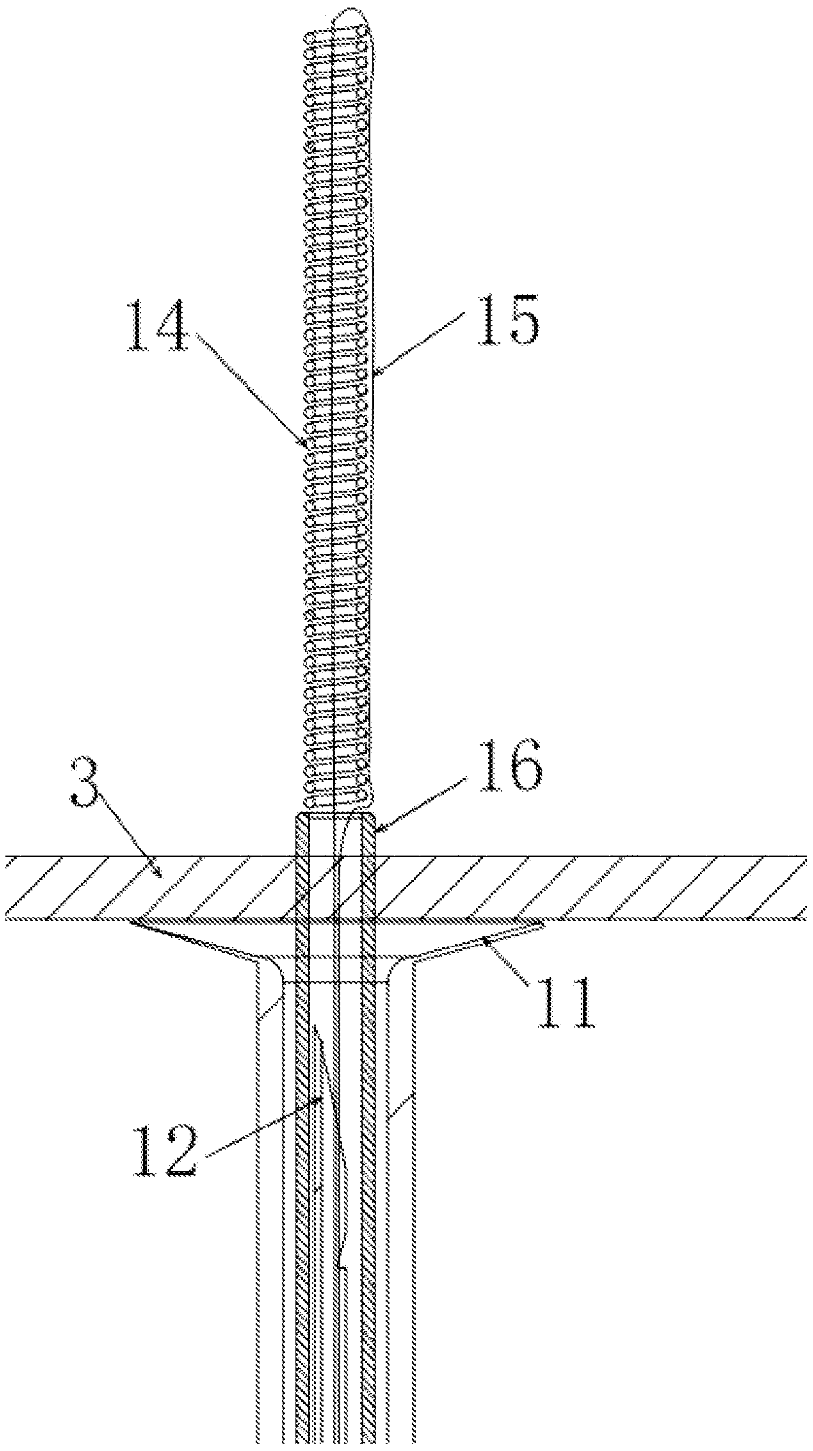
FIG. 4*c* is a schematic diagram of a state that a push sheath is not withdrawn after the puncture needle of the puncturing mechanism in FIG. 1 is withdrawn.
Figure 4D:
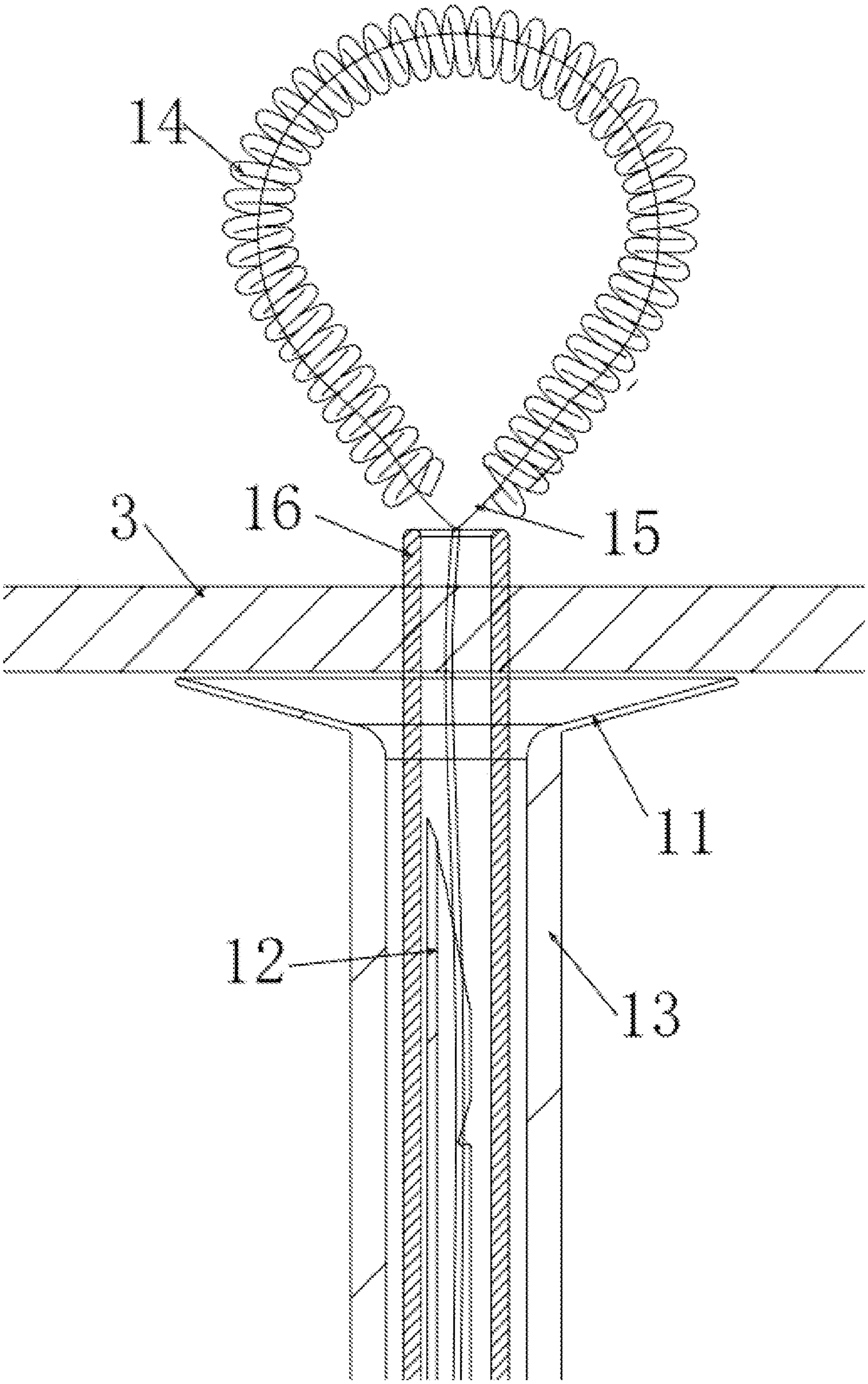
FIG. 4*d* is a schematic diagram of a state after the fixing knots of the puncturing mechanism in FIG. 1 are bent.
Figure 4E:
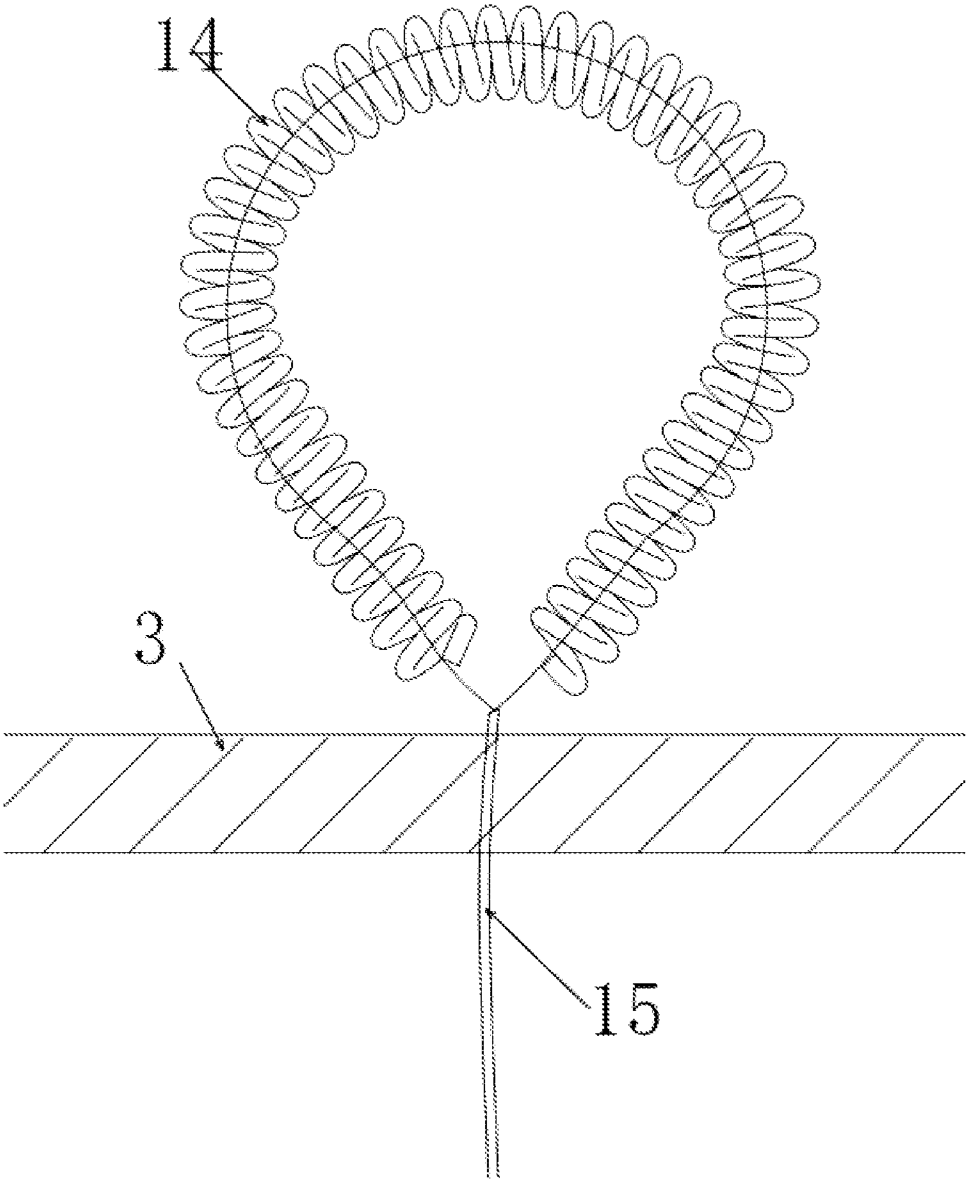
FIG. 4*e* is a schematic diagram of a state after the whole puncturing mechanism in FIG. 1 is withdrawn.

When the fixing knots 14 need to be released, as shown in FIG. 4*a*, an end face of the far end of the outer sheath 13 abuts against the annulus firstly, then the puncture needle and the push sheath 16 slide synchronously towards the far end, the push sheath 16 is used for pushing the fixing knots 14, and it is guaranteed that when the puncture needle and the push sheath 16 are entirely punctured into the mitral valve annulus, the fixing knots 14 are located on a side of a mitral valve close to an atrium, as shown in FIG. 4*b*; due to existence of the notch channel 121, the puncture needle is separated from the fixing knots 14, and the puncture needle is withdrawn firstly, as shown in FIG. 4*c*; then the traction force is applied to the traction wires 15, the fixing knots 14 are bent into a ring shape, as shown in FIG. 4*d*; then the entire outer sheath is withdrawn from the human body, and the fixing knots 14 and the traction wires 15 remain being on the mitral valve annulus, as shown in FIG. 4*e*, to complete a releasing process of the fixing knots 14; and in the released state, the traction wires 15 sleeve side walls of the fixing knots 14, the traction wires 15 are punctured into the annulus, and the fixing knots 14 are pulled by traction of the traction wires 15 to be bent into a ring shape.

Preferably, as shown in FIG. 3, a notch 122 sinking inwards is formed in a side wall of the notch channel 121 of the puncture needle 12; and in the folded state, the far ends of the fixing knots 14 sleeve the notch 122, and the second ends of the traction wires 15 are winded on the outer walls of the fixing knots 14 after passing through the notch 122, so that the fixing knots 14 and the traction wires 15 are conveniently positioned.

Further preferably, as shown in FIG. 1, a fixing head end 11 is arranged on an end face of the far end of the outer sheath 13 and is in a trumpet shape from a proximal end to a far end of the fixing head end, so that an abutting area of the fixing head end 11 on the mitral valve annulus is increased, the annulus may be supported in a direction towards the atrium, and subsequent puncturing of the puncture needle 12 is convenient. Preferably, the fixing head end 11 is made of a medical high molecular material, has certain softness and can protect the annulus from being broken. For example, a nickel-titanium alloy or another memory alloy material may be used.

As for each fixing knot 14, as shown in FIG. 2, the fixing knot 14 may be a spiral tube, namely, a spring-like tube; or as shown in FIG. 1, the fixing knot 14 may be directly a round tube. As for each fixing knot 14, preferably, the fixing knot 14 uses polytetrafluoroethylene (ePTFE) or a nickel-titanium alloy or another medical high molecular or degradable material, has a certain deformation amount for conveniently forming the ring shape after subsequently puncturing in place, and a circular arc surface makes contact with human organ and does not damage the organ making contact with the circular arc surface.

Besides, preferably, the puncture needle 12 of the annulus is made of high-strength metal with a head being ground at a certain angle. The push sheath 16 is made of a metal material or a high molecular material, preferably, the traction wires 15 are made of polytetrafluoroethylene (ePTFE) or another high molecular material.

The ring contraction apparatus for the mitral valve annulus in the optimal implementation of this embodiment may achieve small incision insertion while the heart beats continuously, the dilated annulus is repaired, and a working process is explained by taking annulus repair between the left atrium and the left ventricle.

In an initial state, as shown in FIG. 1 or FIG. 2, the fixing knots 14 and the traction wires 15 are located in the outer sheath 13.

Figure 10:
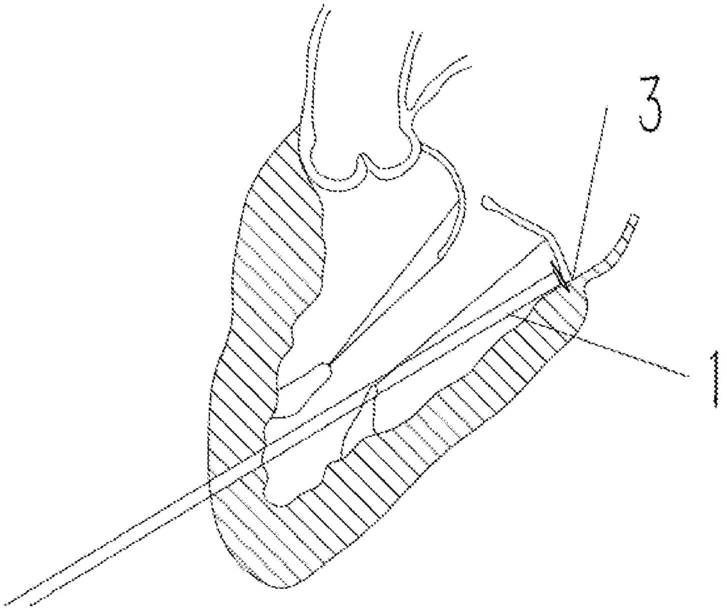
FIG. 10 is a schematic diagram of transapical implantation of a ring contraction apparatus for a mitral valve annulus.

Firstly, as shown in FIG. 10, it enters the left ventricle by cardiac apex puncturing, the outer sheath 13 is delivered to below the mitral valve annulus 3, the fixing head end 11 abuts against the annulus, the annulus is pushed in a direction towards the left atrium, and a puncture point of the annulus is fixed by using an end surface of the far end of the fixing head end after adjusting the direction, as shown in FIG. 4*a*.

Then, the outer sheath 13 remains static, the puncture needle 12, the fixing knots 14, the traction wires 15 and the push sheath 16 push and puncture the annulus together forwards (in the direction towards the left atrium), the puncture needle 12, the traction wires 15 and push sheath 16 are punctured on the annulus, and the fixing knots 14 are located on a side of the left atrium, as shown in FIG. 4*b*; then, the puncture needle 12 is withdrawn firstly, and then a push tube remains pushing the proximal ends of the fixing knots 14, as shown in FIG. 4*c*; afterwards, the traction force is applied to the traction wires 15, so the fixing knots 14 form the ring shape, and a part of the fixing knots 14 located at a left ventricle is knotted, so as to be fixed at an annulus puncture point, as shown in FIG. 4*d*; then, the outer sheath 13 is withdrawn to outside of a cardiac apex to complete puncturing of the first fixing knot 14, as shown in FIG. 4*e*; and the same method is used, another fixing knot 14, namely, the second fixing knot 14, is implanted at the annulus away from the first fixing knot 14 by a distance L1, as shown in FIG. 11*a*.

Afterwards, the locking mechanism 2 is delivered to the annulus by using the conveying mechanism, the outer tube 24 is conveyed to the mitral valve annulus 3 through transapical puncture, the outer tube 24 stops moving, the hanging sheath 23 moves to push the locking body 21 to a bottom of the mitral valve annulus 3, the end parts of the traction wires 15 of the two adjacent fixing knots 14 pass through the locking hole 27 via the first channel of the locking body 21 to extend towards the proximal end; then, the traction force is applied to the traction wires 15 through three-dimensional ultrasound and contrast navigation, the distance between the two annulus fixing knots 14 is adjusted in real time till reflux disappears, for example, the distance between the two fixing knots 14 is finally adjusted to L2, a circumferential length of the mitral valve annulus 3 is shortened, and thus, narrowing of the annulus is achieved; at the moment, the locking plug 22 is pushed to the farthest end of the locking body 21 through the push inner tube 25, the elastic piece plays a role in blocking the locking plug 22, the traction wires 15 are fixed onto the locking body 21, ring contraction of the mitral valve annulus 3 is completed once, as shown in FIG. 11*b*; and finally, the outer tube 24, the hanging sheath 23 and the push inner tube 25 are entirely withdrawn from the human body.

Figure 12:
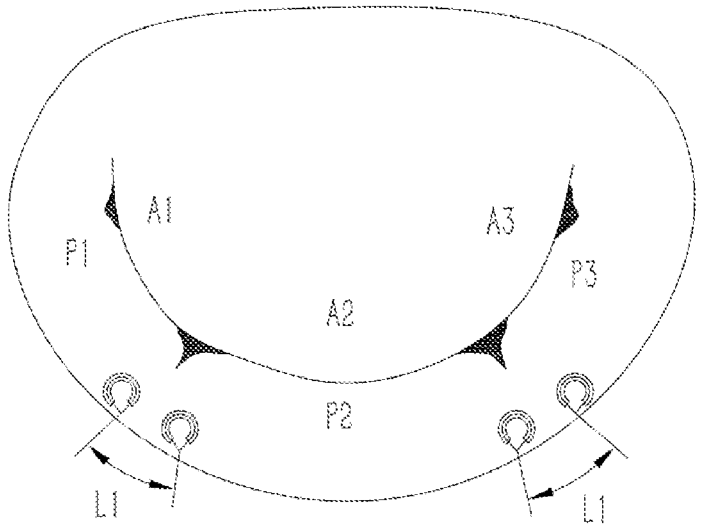
FIG. 12 is a schematic diagram of a ring contraction apparatus for a mitral valve annulus being located at an atrium surface annulus.
Figure 13:
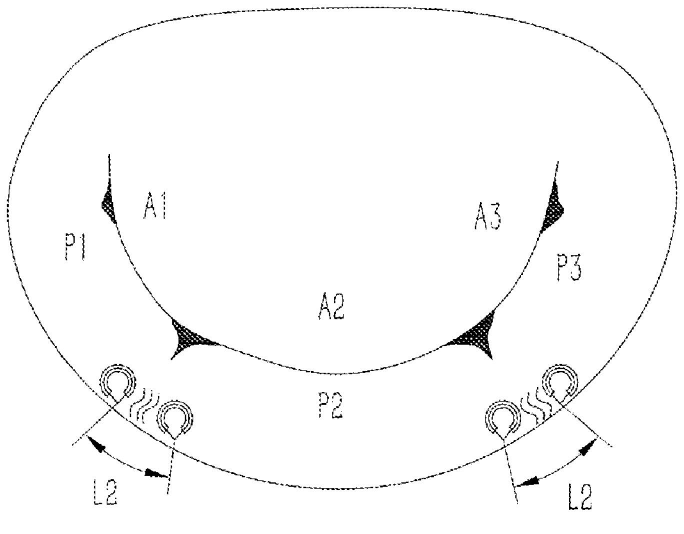
FIG. 13 is a schematic diagram of an annulus ring contraction state after a ring contraction apparatus for a mitral valve annulus is locked.

As shown in FIG. 12 and FIG. 13, a plurality of pairs of fixing knots 14 may be implanted on the mitral valve annulus 3 in the above same manner to further reduce a size of the annulus.

As for the set number of fixing mechanisms, the number of fixing mechanisms is an even number, a pair of fixing mechanisms may implement a ring contraction function of the annulus, and the specific set number is not limited and may be selected according to actual demands.

Besides, a knotting position of the two ends of the traction wires 15 of each fixing knot 14 above is close to a position of the annulus, and the traction wires 15 may also be knotted and fixed at a cardiac apex according to a lesion of a patient to complete implantation and securing of the ring contraction apparatus.

Apparently, the above embodiments are merely for clearly describing the examples but not for limiting the implementations. Those ordinarily skilled in the art may also make modifications or variations in other different forms based on the above description. All implementations do not need to be and cannot be exhaustively cited here. Apparent modifications or variations derived from this still fall within the protection scope of the present disclosure.

The invention claimed is:

1. A ring contraction apparatus for a mitral valve annulus, comprising at least two fixing mechanisms; wherein each fixing mechanism comprises a fixing knot and a traction wire, the traction wire is mounted on the fixing knot, and two ends of the traction wire are located outside a proximal end of the fixing knot;

a puncturing mechanism, used for puncturing the fixing knot and the traction wire of any one of the fixing mechanisms into the annulus, so that the fixing knot is located on one side of the annulus and two ends of the traction wire are located on the other side of the annulus, wherein the traction wires of two adjacent fixing mechanisms are driven by a traction force to approach each other so as to shorten a distance between two adjacent fixing knots; and a locking mechanism, used for locking ends of the traction wires in the two adjacent fixing mechanisms onto the annulus in a case that the traction wires of the two adjacent fixing mechanism are pulled in place; wherein the locking mechanism comprises:

a locking body, having a first channel extending in a length direction of the locking body;

a locking plug, inserted into the first channel so as to clamp the traction wires between the locking plug and the locking body; and a conveying mechanism comprising an outer tube, a hanging sheath slidably arranged in the outer tube and a push inner tube slidably arranged in the hanging sheath, wherein a far end of the hanging sheath is detachably connected with a proximal end of the locking body, and a far end of the push inner tube is inserted into or is in sleeving fit with a proximal end of the locking plug; and both the locking body and the locking plug are located in the outer tube before the locking body is released.

2. The ring contraction apparatus for the mitral valve annulus of claim 1, wherein a locking hole through which the ends of the traction wires pass is formed in a side wall of the locking body.

3. The ring contraction apparatus for the mitral valve annulus of claim 2, wherein a first mounting hole is also arranged in the side wall of the locking body;

the locking mechanism further comprises at least one elastomer, a proximal end of the elastomer is formed in the first mounting hole, and a far end of the elastomer tends to extend into the first channel under an action of its own deformation amount; and the elastomer swings towards an inside of the first mounting hole under an extrusion force of an outer wall of the locking plug in a case that the locking plug is inserted towards the first channel, and after the locking plug crosses the far end of the elastomer, the elastomer is restored and the far end of the elastomer is blocked onto the locking plug.

4. The ring contraction apparatus for the mitral valve annulus of claim 2, wherein the locking mechanism further comprises a conveying mechanism; the conveying mechanism comprises an outer tube, a hanging sheath slidably arranged in the outer tube and a push inner tube slidably arranged in the hanging sheath;

a far end of the hanging sheath is detachably connected with a proximal end of the locking body, and a far end of the push inner tube is inserted into or is in sleeving fit with a proximal end of the locking plug; and both the locking body and the locking plug are located in the outer tube before the locking body is released.

5. The ring contraction apparatus for the mitral valve annulus of claim 2, wherein the puncturing mechanism comprises:

an outer sheath;

a puncture needle, slidably arranged in the outer sheath, wherein a notch channel extending in a length direction of the puncture needle is arranged on an outer wall of a far end of the puncture needle; and a push sheath, slidably arranged in the outer sheath and sleeving the puncture needle; wherein the fixing knots have a folded state of being folded into the outer sheath and a released state of being punctured onto the annulus;

in the folded state, the fixing knots sleeve an outer wall of the notch channel of the puncture needle, a proximal end of the puncture needle and a far end of the push sheath are distributed oppositely, a first end of each traction wire is located in the notch channel, and a second end of the traction wire passes through the notch channel, then is wound onto an outer wall of the fixing knot from a far end of the fixing knot and extends into the puncture needle via a proximal end of the notch channel so as to overlap the first end and the second end; and in the released state, the traction wires sleeve side walls of the fixing knots and are punctured onto the annulus, and the fixing knots bend to form a ring under traction of the traction wires.

6. The ring contraction apparatus for the mitral valve annulus of claim 1, wherein a first mounting hole is also arranged in the side wall of the locking body;

the locking mechanism further comprises at least one elastomer, a proximal end of the elastomer is formed in the first mounting hole, and a far end of the elastomer tends to extend into the first channel under an action of its own deformation amount; and the elastomer swings towards an inside of the first mounting hole under an extrusion force of an outer wall of the locking plug in a case that the locking plug is inserted towards the first channel, and after the locking plug crosses the far end of the elastomer, the elastomer is restored and the far end of the elastomer is blocked onto the locking plug.

7. The ring contraction apparatus for the mitral valve annulus of claim 6, wherein the locking plug comprises a base and a first annular boss formed on a periphery of a far end of the base, and the first annular boss applies an extrusion force to the elastomer; and the far end of the elastomer is blocked onto a side of a proximal end of the first annular boss in a case that the elastomer is restored.

8. The ring contraction apparatus for the mitral valve annulus of claim 7, wherein a second annular boss protruding inwards is arranged on an inner wall of a far end of the locking body;

a far end of the first annular boss is maintained between the second annular boss and the elastomer under blocking of the second annular boss; and/or the elastomer is an elastic piece.

9. The ring contraction apparatus for the mitral valve annulus of claim 8, wherein the locking mechanism further comprises a conveying mechanism; the conveying mechanism comprises an outer tube, a hanging sheath slidably arranged in the outer tube and a push inner tube slidably arranged in the hanging sheath;

a far end of the hanging sheath is detachably connected with a proximal end of the locking body, and a far end of the push inner tube is inserted into or is in sleeving fit with a proximal end of the locking plug; and both the locking body and the locking plug are located in the outer tube before the locking body is released.

10. The ring contraction apparatus for the mitral valve annulus of claim 8, wherein the puncturing mechanism comprises:

an outer sheath;

a puncture needle, slidably arranged in the outer sheath, wherein a notch channel extending in a length direction of the puncture needle is arranged on an outer wall of a far end of the puncture needle; and a push sheath, slidably arranged in the outer sheath and sleeving the puncture needle; wherein the fixing knots have a folded state of being folded into the outer sheath and a released state of being punctured onto the annulus;

in the folded state, the fixing knots sleeve an outer wall of the notch channel of the puncture needle, a proximal end of the puncture needle and a far end of the push sheath are distributed oppositely, a first end of each traction wire is located in the notch channel, and a second end of the traction wire passes through the notch channel, then is wound onto an outer wall of the fixing knot from a far end of the fixing knot and extends into the puncture needle via a proximal end of the notch channel so as to overlap the first end and the second end; and in the released state, the traction wires sleeve side walls of the fixing knots and are punctured onto the annulus, and the fixing knots bend to form a ring under traction of the traction wires.

11. The ring contraction apparatus for the mitral valve annulus of claim 7, wherein the locking mechanism further comprises a conveying mechanism; the conveying mechanism comprises an outer tube, a hanging sheath slidably arranged in the outer tube and a push inner tube slidably arranged in the hanging sheath;

a far end of the hanging sheath is detachably connected with a proximal end of the locking body, and a far end of the push inner tube is inserted into or is in sleeving fit with a proximal end of the locking plug; and both the locking body and the locking plug are located in the outer tube before the locking body is released.

12. The ring contraction apparatus for the mitral valve annulus of claim 5, wherein the puncturing mechanism comprises:

an outer sheath;

a puncture needle, slidably arranged in the outer sheath, wherein a notch channel extending in a length direction of the puncture needle is arranged on an outer wall of a far end of the puncture needle; and a push sheath, slidably arranged in the outer sheath and sleeving the puncture needle;

wherein the fixing knots have a folded state of being folded into the outer sheath and a released state of being punctured onto the annulus;

in the folded state, the fixing knots sleeve an outer wall of the notch channel of the puncture needle, a proximal end of the puncture needle and a far end of the push sheath are distributed oppositely, a first end of each traction wire is located in the notch channel, and a second end of the traction wire passes through the notch channel, then is wound onto an outer wall of the fixing knot from a far end of the fixing knot and extends into the puncture needle via a proximal end of the notch channel so as to overlap the first end and the second end; and in the released state, the traction wires sleeve side walls of the fixing knots and are punctured onto the annulus, and the fixing knots bend to form a ring under traction of the traction wires.

13. The ring contraction apparatus for the mitral valve annulus of claim 6, wherein the locking mechanism further comprises a conveying mechanism; the conveying mechanism comprises an outer tube, a hanging sheath slidably arranged in the outer tube and a push inner tube slidably arranged in the hanging sheath;

a far end of the hanging sheath is detachably connected with a proximal end of the locking body, and a far end of the push inner tube is inserted into or is in sleeving fit with a proximal end of the locking plug; and both the locking body and the locking plug are located in the outer tube before the locking body is released.

14. The ring contraction apparatus for the mitral valve annulus of claim 6, wherein the puncturing mechanism comprises:

an outer sheath;

a puncture needle, slidably arranged in the outer sheath, wherein a notch channel extending in a length direction of the puncture needle is arranged on an outer wall of a far end of the puncture needle; and a push sheath, slidably arranged in the outer sheath and sleeving the puncture needle; wherein the fixing knots have a folded state of being folded into the outer sheath and a released state of being punctured onto the annulus;

in the folded state, the fixing knots sleeve an outer wall of the notch channel of the puncture needle, a proximal end of the puncture needle and a far end of the push sheath are distributed oppositely, a first end of each traction wire is located in the notch channel, and a second end of the traction wire passes through the notch channel, then is wound onto an outer wall of the fixing knot from a far end of the fixing knot and extends into the puncture needle via a proximal end of the notch channel so as to overlap the first end and the second end; and in the released state, the traction wires sleeve side walls of the fixing knots and are punctured onto the annulus, and the fixing knots bend to form a ring under traction of the traction wires.

15. The ring contraction apparatus for the mitral valve annulus of claim 1, wherein the puncturing mechanism comprises:

an outer sheath;

a puncture needle, slidably arranged in the outer sheath, wherein a notch channel extending in a length direction of the puncture needle is arranged on an outer wall of a far end of the puncture needle; and a push sheath, slidably arranged in the outer sheath and sleeving the puncture needle; wherein the fixing knots have a folded state of being folded into the outer sheath and a released state of being punctured onto the annulus;

in the folded state, the fixing knots sleeve an outer wall of the notch channel of the puncture needle, a proximal end of the puncture needle and a far end of the push sheath are distributed oppositely, a first end of each traction wire is located in the notch channel, and a second end of the traction wire passes through the notch channel, then is wound onto an outer wall of the fixing knot from a far end of the fixing knot and extends into the puncture needle via a proximal end of the notch channel so as to overlap the first end and the second end; and in the released state, the traction wires sleeve side walls of the fixing knots and are punctured onto the annulus, and the fixing knots bend to form a ring under traction of the traction wires.

16. The ring contraction apparatus for the mitral valve annulus of claim 15, wherein a notch sinking inwards is formed in a side wall of the notch channel of the puncture needle; and in the folded state, the far ends of the fixing knots sleeve the notch, and the second ends of the traction wires are wound on the outer walls of the fixing knots after passing through the notch.

17. The ring contraction apparatus for the mitral valve annulus according to claim 15, wherein each fixing knot is in a spiral shape or a round tube shape; and/or a fixing head end is arranged on an end face of a far end of the outer sheath and is in a trumpet shape from its proximal end to its far end.

* * * * *